(12) United States Patent
Fehling

(10) Patent No.: US 9,795,368 B2
(45) Date of Patent: Oct. 24, 2017

(54) RETRACTOR FOR CRANIAL SURGERY

(71) Applicant: Fehling Medical Corporation, Acworth, GA (US)

(72) Inventor: Guido Fehling, Karlstein (DE)

(73) Assignee: Fehling Instruments GmbH & Co. KG, Karlstein (DE)

( * ) Notice: Subject to any disclaimer, the term of this patent is extended or adjusted under 35 U.S.C. 154(b) by 0 days.

(21) Appl. No.: 14/542,777

(22) Filed: Nov. 17, 2014

(65) Prior Publication Data

US 2017/0007226 A1    Jan. 12, 2017

(30) Foreign Application Priority Data

Nov. 18, 2013 (DE) .................... 20 2013 105 202 U

(51) Int. Cl.
*A61B 1/32* (2006.01)
*A61B 17/02* (2006.01)
(Continued)

(52) U.S. Cl.
CPC .......... *A61B 17/0206* (2013.01); *A61B 17/02* (2013.01); *A61L 31/022* (2013.01);
(Continued)

(58) Field of Classification Search
CPC .................... A61B 17/0206; Y10T 403/32254
See application file for complete search history.

(56) References Cited

U.S. PATENT DOCUMENTS 266,804 A * 10/1882 Fraser ................... B02C 2/06
                                                           241/209
2,681,818 A *  6/1954 Rosan ................... F16B 39/28
                                                           403/83
(Continued)

FOREIGN PATENT DOCUMENTS

CN        2137935 Y       9/1992
DE     299 18 536 U1    10/1999
WO    WO 01/50946 A2     7/2001

OTHER PUBLICATIONS

European Search Report dated Apr. 8, 2015 for corresponding European application 14193616.1.
(Continued)

*Primary Examiner* — Ellen C Hammond
*Assistant Examiner* — Stuart S Bray
(74) *Attorney, Agent, or Firm* — Juneau & Mitchell

(57) ABSTRACT

A retractor, particularly for cranial surgery, having two articulated parts that can be pivoted relative to each other about a rotary axis, wherein each articulated part has a handle part on the proximal end and a retracting element on the distal end, wherein a section of each articulated part spans a plane and wherein a clamping arm is arranged on at least one of the articulated parts. The clamping arm has multiple tensioning elements, which are threaded onto a traction cable and engage with each other and can be tilted and rotated relative to each other, wherein the clamping arm is arranged about a pivotal axis and the pivotal axis is connected to the articulated part by an arm arranged in a plane, wherein the arm is aligned outwards from the articulated part and the pivot axis is positioned in the plane at a distance from the articulated part.

12 Claims, 3 Drawing Sheets

(51) Int. Cl.
*A61L 31/02* (2006.01)
*A61L 31/14* (2006.01)
*A61B 17/28* (2006.01)
*A61B 17/00* (2006.01)
*A61B 90/50* (2016.01)
*A61B 90/10* (2016.01)
*A61B 90/57* (2016.01)

(52) U.S. Cl.
CPC ........... *A61L 31/14* (2013.01); *A61B 17/2812* (2013.01); *A61B 90/50* (2016.02); *A61B 2017/00867* (2013.01); *A61B 2017/00946* (2013.01); *A61B 2017/0287* (2013.01); *A61B 2017/2837* (2013.01); *A61B 2090/103* (2016.02); *A61B 2090/571* (2016.02); *A61L 2400/16* (2013.01)

(56) References Cited

U.S. PATENT DOCUMENTS

| | | | | |
|---|---|---|---|---|
| 2,928,693 | A * | 3/1960 | Cannon, Jr. | F41F 5/04 279/100 |
| 4,491,183 | A * | 1/1985 | Anderson | A01B 39/166 172/100 |
| 4,930,932 | A | 6/1990 | LeVahn | |
| 5,759,206 | A * | 6/1998 | Bassett | A61F 2/76 403/113 |
| 5,957,835 | A * | 9/1999 | Anderson | A61B 17/0206 600/201 |
| 6,036,641 | A * | 3/2000 | Taylor | A61B 17/00234 600/229 |
| 6,113,536 | A * | 9/2000 | Aboul-Hosn | A61B 17/0206 600/227 |
| 6,168,601 | B1 | 1/2001 | Martini | |
| 6,196,568 | B1 * | 3/2001 | Stevens | A61G 5/12 280/304.1 |
| 6,468,207 | B1 | 10/2002 | Fowler, Jr. | |
| 6,887,198 | B2 * | 5/2005 | Phillips | A61B 17/02 600/227 |
| 9,049,989 | B2 * | 6/2015 | Crenshaw | A61B 5/0051 |
| 2001/0041827 | A1 * | 11/2001 | Spence | A61B 17/02 600/201 |
| 2002/0095139 | A1 * | 7/2002 | Keogh | A61B 17/0206 606/1 |
| 2003/0069479 | A1 | 4/2003 | Phillips et al. | |
| 2003/0149341 | A1 * | 8/2003 | Clifton | A61B 17/0206 600/210 |
| 2004/0055125 | A1 * | 3/2004 | Guenst | A61B 17/0206 28/107 |
| 2004/0096263 | A1 * | 5/2004 | Aquino | B64D 11/003 403/24 |
| 2004/0158286 | A1 * | 8/2004 | Roux | A61B 17/0206 606/205 |
| 2005/0010197 | A1 * | 1/2005 | Lau | A61B 17/0206 606/1 |
| 2005/0215851 | A1 * | 9/2005 | Kim | A61B 17/02 600/37 |
| 2005/0234304 | A1 * | 10/2005 | Dewey | A61B 17/0206 600/210 |
| 2007/0129634 | A1 * | 6/2007 | Hickey | A61B 8/00 600/439 |
| 2007/0161988 | A1 * | 7/2007 | Drewry | A61B 17/7005 606/86 A |
| 2008/0221394 | A1 * | 9/2008 | Melkent | A61B 17/0206 600/201 |
| 2009/0192360 | A1 * | 7/2009 | Riess | A61B 17/02 600/210 |
| 2010/0222644 | A1 * | 9/2010 | Sebastian | A61B 17/0206 600/228 |
| 2011/0028797 | A1 * | 2/2011 | Yee | A61B 17/0206 600/231 |
| 2012/0067164 | A1 * | 3/2012 | Su | B25G 1/06 74/575 |
| 2012/0157788 | A1 * | 6/2012 | Serowski | A61B 17/0206 600/229 |
| 2014/0005484 | A1 * | 1/2014 | Charles | A61B 17/02 600/201 |
| 2014/0105670 | A1 * | 4/2014 | Plomteux | F16C 11/10 403/83 |
| 2014/0308063 | A1 * | 10/2014 | Gold | G01S 7/4004 403/83 |
| 2016/0015459 | A1 * | 1/2016 | Greenberg | A61B 17/0206 600/218 |

OTHER PUBLICATIONS

Search report (untranslated) of GPTO dated Aug. 27, 2014 for corresponding German application 20 2013 105 202.7.

* cited by examiner

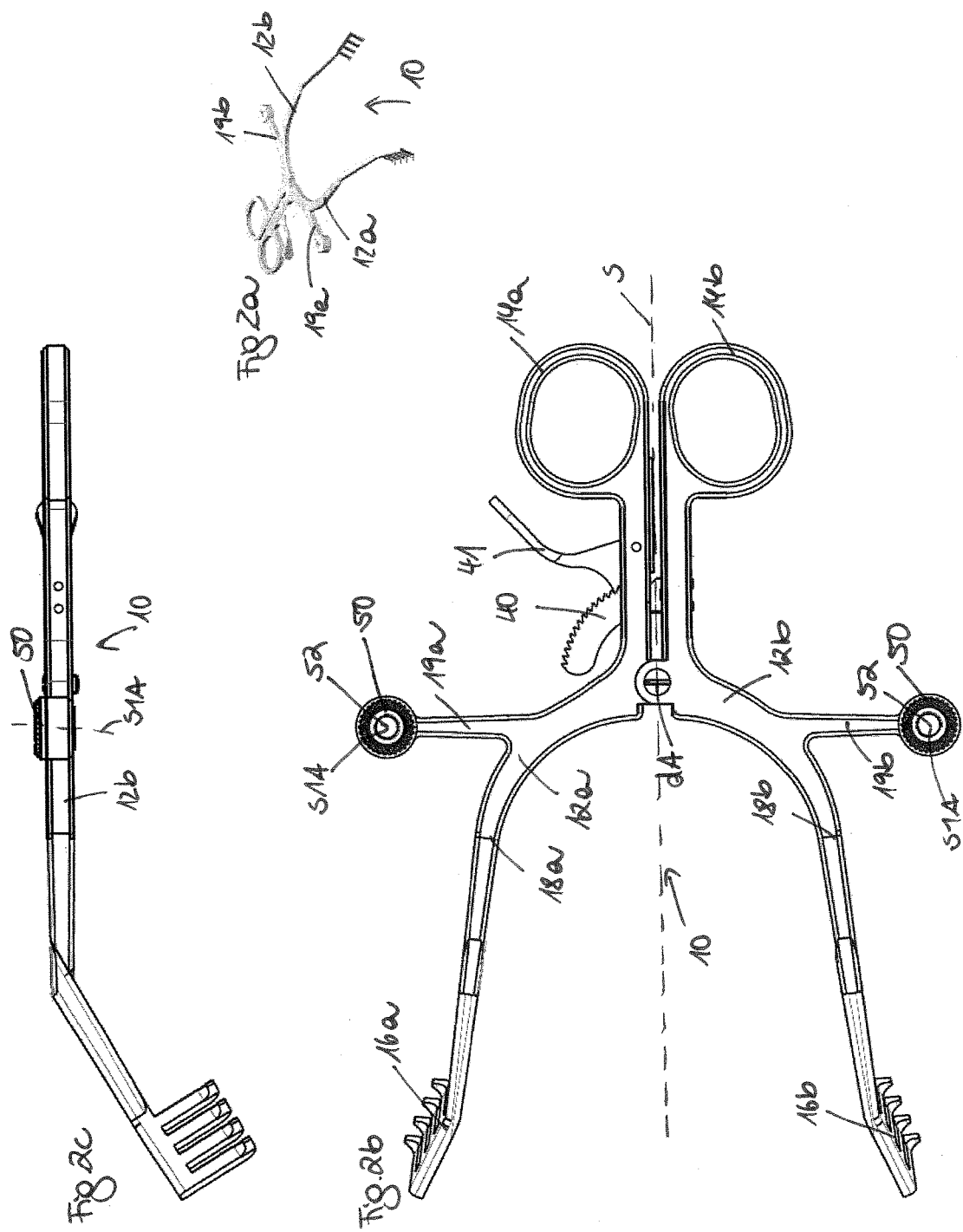

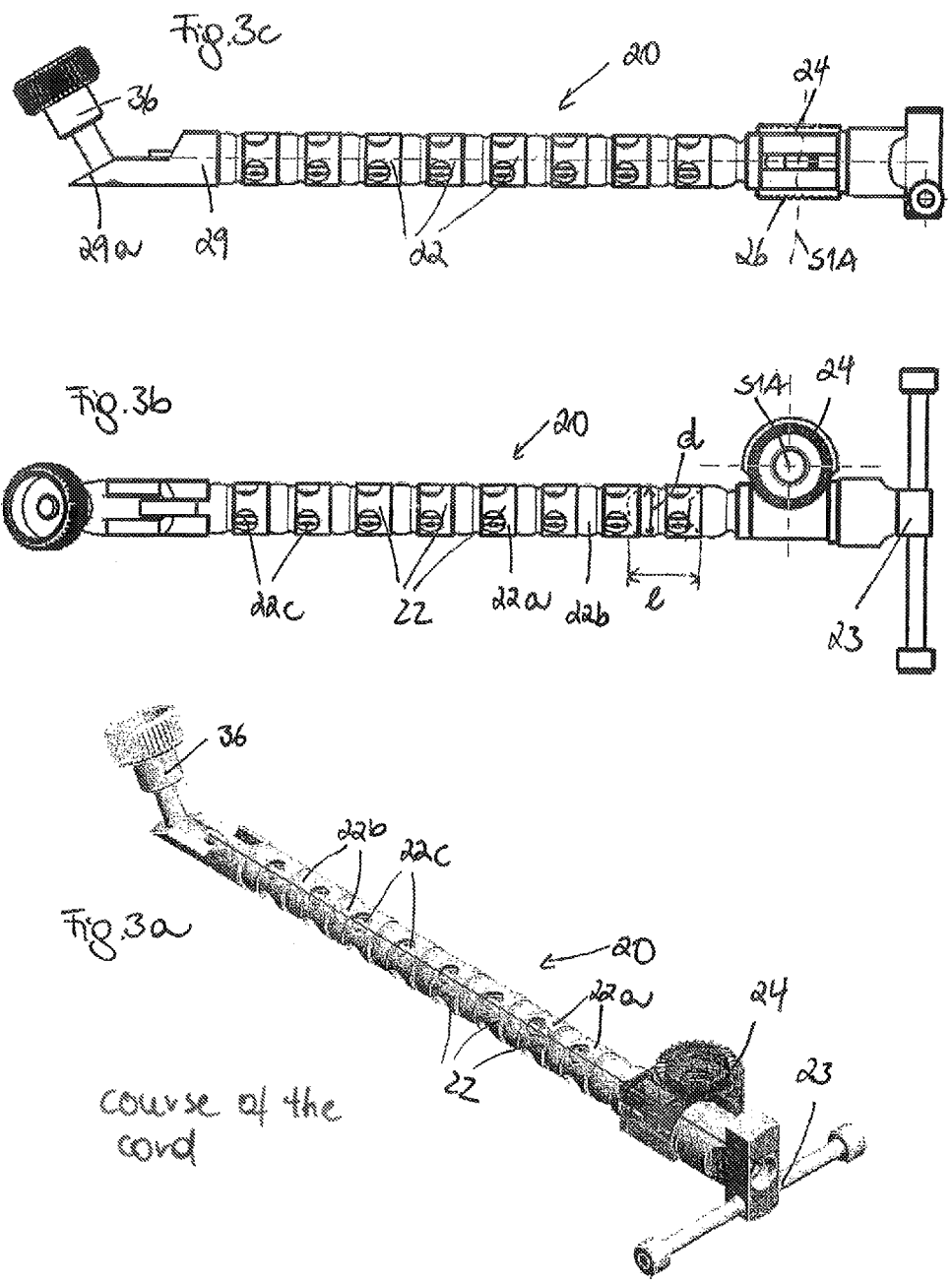

RETRACTOR FOR CRANIAL SURGERY

CROSS REFERENCE TO RELATED APPLICATIONS

This patent application claims priority to German Patent Application 20 2013 105 202.7, filed on Nov. 18, 2013.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The present invention relates to a retractor, preferably for cranial surgery.

Background of the Invention

Retractors are known, in particular for cranial surgery, having two articulated parts, which can be pivoted relative to each other about a rotary axis, wherein each articulated part has a handle part on the proximal end and a retracting element on the distal end, wherein a section of each articulated part spans a plane and wherein a clamping arm is arranged on at least one of the articulated parts, wherein the clamping arm has a plurality of tensioning elements, which are threaded onto a traction cable and which engage with each other in sections and can be tilted and/or rotated relative to each other. Soft tissue is usually retracted using the retracting elements, whilst brain spatulas are generally attached to the clamping arms in order to hold tissue, particularly inside the cranium, in a desired position.

The connection between the clamping arm and the articulated part is often not tight enough in the known retractors and/or not variable to the extent required for the selected use.

The objective of the invention is therefore to provide a retractor, in particular for cranial surgery, which is more flexible, and preferably, can be used more safely.

The objective of the invention is solved by a retractor, in particular for cranial surgery, having the features described herein below.

BRIEF SUMMARY OF THE INVENTION

In a preferred embodiment, a retractor, comprising two articulated parts that can be pivoted relative to each other about a rotary axis, wherein each articulated part has a handle part on the proximal end and a retracting element on the distal end, wherein a section of each articulated part spans a plane and wherein a clamping arm is arranged on at least one of the articulated parts. The clamping arm has a plurality of tensioning elements, which are threaded onto a traction cable and which engage with each other in sections and can be tilted and/or rotated relative to each other, wherein the clamping arm is pivotably arranged about a pivotal axis and the pivotal axis is connected to the articulated part by means of an arm arranged in a plane, wherein the arm is aligned outwards from the articulated part and consequently the pivotal axis is positioned in the plane at a distance from the articulated part.

In another preferred embodiment, the retractor as described herein, wherein the tensioning elements have a length and a diameter, wherein the ratio between the diameter and the length is between 1:1 and 2:3.

In another preferred embodiment, the retractor as described herein, wherein each tensioning element has a cylindrical section and a semi-spherical section, wherein a semi-spherical section of a tensioning element engages in a cylindrical section of another tensioning element.

In another preferred embodiment, the retractor as described herein, wherein the tensioning elements have one or more windows, which windows are arranged in the cylindrical section.

In another preferred embodiment, the retractor as described herein, wherein the clamping arm has a sprocket running about the pivotal axis, which can be attached to a sprocket arranged on the arm running about the pivotal axis.

In another preferred embodiment, the retractor as described herein, wherein the clamping arm has two sprockets arranged parallel to each other running about the pivotal axis, and the teeth of said sprockets point in opposite directions.

In another preferred embodiment, the retractor as described herein, further comprising wherein a holder for a brain spatula is arranged on the distal end of the clamping arm.

In another preferred embodiment, the retractor as described herein, wherein the distal end of the clamping arm is beveled and a bearing surface of the holder abuts the beveled surface of the distal end of the clamping arm and is arranged in a rotatably mounted manner about a rotary axis which vertically intersects the bearing surface.

In another preferred embodiment, the retractor as described herein, wherein the brain spatula is made from a shape memory material, such as nickel titanium.

In another preferred embodiment, the retractor as described herein, wherein a locking mechanism, preferably a ratchet lock, is arranged between both articulated parts.

In another preferred embodiment, the retractor as described herein, wherein a locking mechanism, preferably a ratchet lock, is arranged between both handle parts.

In another preferred embodiment, the retractor as described herein, wherein the retracting element is configured as retracting prongs and is arranged at an angle to the plane.

BRIEF DESCRIPTION OF THE DRAWINGS

FIG. 2b is a line drawing evidencing a top view of the retractor as per FIG. 2a, FIG. 2c is a line drawing evidencing a side view of the retractor as per FIG. 2a, FIG. 3a is a line drawing evidencing a perspective view of a clamping arm of the retractor as per FIG. 1a, FIG. 3b is a line drawing evidencing a top view of the clamping arm as per FIG. 3a and FIG. 3c is a line drawing evidencing a side view of the clamping arm as per FIG. 3a.

DETAILED DESCRIPTION OF THE INVENTION

Figure 1D:
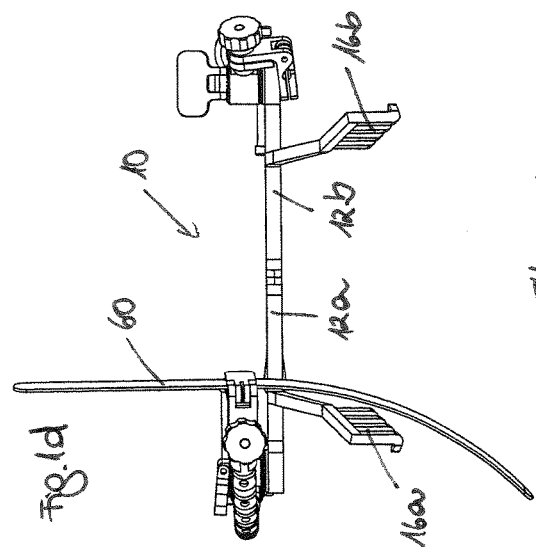
FIG. 1a is a line drawing evidencing a perspective view of an embodiment of a retractor as per the invention with clamping arms arranged thereon.
FIG. 1b is a line drawing evidencing a top view of the arrangement as per FIG. 1a, FIG. 1c is a line drawing evidencing a side view of the arrangement as per FIG. 1a, FIG. 1d is a line drawing evidencing a front view of the arrangement as per FIG. 1a, FIG. 2a is a line drawing evidencing a perspective view of the retractor as per FIG. 1a without clamping arms arranged thereon.

The retractor as per the invention, in particular for cranial surgery, having two articulated parts that can be pivoted relative to each other about a rotary axis, wherein each articulated part has a handle part on the proximal end and a retracting element on the distal end, wherein a section of each articulated part spans a plane and wherein a clamping arm is arranged on at least one of the articulated parts, wherein the clamping arm has a plurality of tensioning elements, which are threaded onto a traction cable and which engage with each other in sections and can be tilted and/or rotated relative to each other, is characterized in that the clamping arm is swivel-mounted about a pivot axis and the pivot axis is connected to the articulated part by means of an arm arranged in the plane, wherein the arm is directed outwards from the articulated part and consequently the pivot axis is spaced in the plane to the articulated part.

Displacement of the pivotal axis outwards from the articulated part by means of the arm allows the same regions between both articulated parts to be reached with the distal end of the clamping arm due to less bending of the clamping arm or arrangement of the clamping arm in larger bending radiuses than in conventional retractors. Since the clamping arm needs less bending or can be used with larger bending radiuses, this makes the clamping process easier and enables stable fixing of the clamping arm. More particularly, the greater distance between the pivotal axis on which the clamping arm is attached and the rotary axis between both articulated parts enables unobstructed positioning and contraction of the respective clamping arm.

Advantageously, the arm is fixedly, in particular integrally, formed, and is arranged at the hinge part.

Advantageously, the tensioning elements have a length and a diameter wherein the ratio between the diameter and the length is between 1:1 and 2:3. The tensioning elements can thus be configured shorter than in a conventional manner which enables a more flexible arrangement of the clamping arm.

An advantageous embodiment makes provision that the tensioning elements each have a cylindrical section and a semi-spherical section, wherein a semi-spherical section of a tensioning element engages with a cylindrical section of another tensioning element. This achieves a surface of the clamping arm that is as smooth as possible or is virtually enclosed even when bending the clamping arm, and which, more particularly, has hardly any edges or corners that could lead to a risk of injury.

According to a particularly preferred embodiment of the invention, the tensioning elements have at least one, preferably a plurality, of windows, which are arranged preferably in the cylindrical section. This enables thorough cleaning of the tensioning elements of the clamping arm.

In a particularly preferred embodiment, the clamping arm has a sprocket running about the pivotal axis, which is attachable to a sprocket running about the pivotal axis arranged on the arm. These intermeshing sprockets enable a stable, more particularly fixed angled, placement of the clamping arm on the articulated part in a desired position and prevent unwanted rotation of the clamping arm about the pivotal axis. Secondly, the sprockets enable the clamping arm to be positioned at various angles about the pivotal axis relative to the sprocket arranged on the arm, which enables flexible use. If the teeth are finer, this enables in particular virtually any angle coupling between the clamping arm and the respective articulated part. In addition, both sprockets enable a space-saving connection since, for example, both sprockets can be screwed together by means of a central bore hole.

Advantageously, the clamping arm has two sprockets arranged parallel to each other running about the pivotal axis, the teeth of which sprockets point in the opposite direction, which increases flexibility even further, particularly such that the clamping arm can be used on both articulated parts of the retractor.

Preferably, a holder for a brain spatula is arranged at the distal end of the clamping arm. This further increases the flexibility of the retractor according to the invention.

Preferably, the distal end of the clamping arm is beveled and a bearing surface of the holder is either rigidly or rotatably mounted on the beveled surface of the distal end of the clamping arm about a rotary axis which vertically intersects the beveled surface to the bearing surface. When the holder rotates around the beveled distal end of the clamping arm, this enables the orientation of a retracting element, such as a brain spatula, arranged in the holder, in different spatial directions.

A preferred embodiment of the invention makes the provision that the brain spatula is made from a shape memory material, such as nickel titanium, which can be shaped, particularly at room temperature, arbitrarily depending on the surgical purpose and regains its original shape during processing under the thermal influence of hot rinsing water. This improves its flexible uses and enables targeted manageability of the retractor as well as an extension of the service life of the brain spatula.

Preferably, a locking mechanism, preferably a ratchet lock, is arranged between both articulated parts, more particularly between both handle parts, in order to fix both articulated parts at a desired angle relative to each other.

Advantageously, the retracting element is configured as retracting prongs, and preferably arranged at an angle to the plane in order to enable the reliable retraction of tissue.

DETAILED DESCRIPTION OF THE FIGURES

Figure 1A:
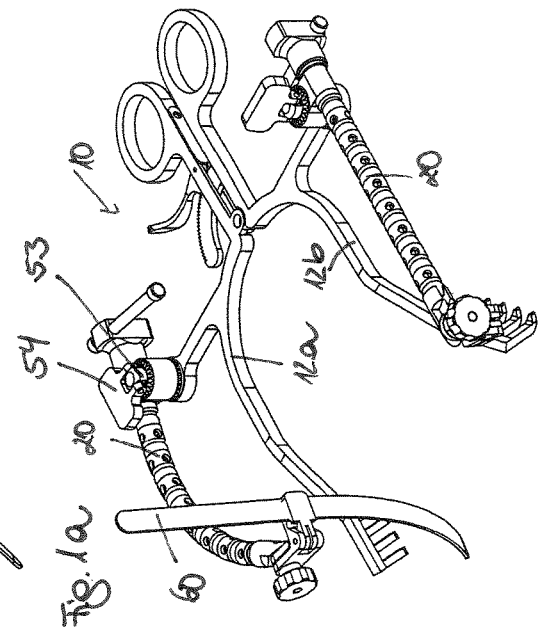
Figure 1C:
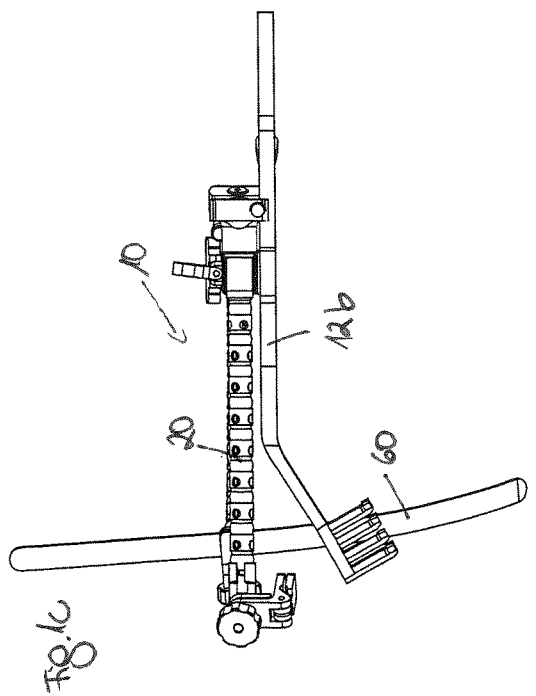
Figure 1B:
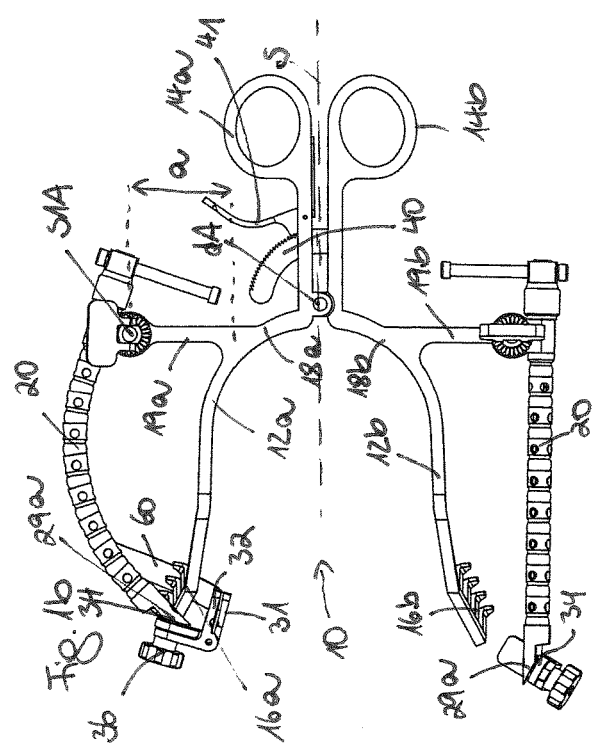

FIGS. 1a to 1d show an embodiment of a retractor 10 as per the invention having two clamping arms 20 arranged thereon. FIGS. 2a to 2c show the retractor 10 as per FIGS. 1a to 1d without the clamping arms 20 arranged thereon and FIGS. 3a to 3c show various views of the clamping arms 20 of the retractor as per FIGS. 1a to 1d.

The retractor 10 has two articulated parts 12a, 12b arranged in a pivotable manner about a rotary axis dA in a rotatable manner, each of which articulated parts has a handle part 14a, 14b on the proximal end and a retracting element 16a, 16b on the distal end. Here the articulated parts 12a, 12b are arranged together in particular such that they do not cross, and consequently when both articulated parts 12a, 12b are closed against each other the retracting elements 16a, 16b are pushed apart from each other. A section 18a, 18b spanning a plane is arranged between the handle parts 14a, 14b and the retracting elements 16a, 16b. More particularly, the handle parts 14a, 14b also lie in this plane. The retracting elements 16a, 16b are at an angle to the plane in one embodiment. The retracting elements 16a, 16b can be configured particularly as retracting prongs.

A symmetrical axis S can be formed between both articulated parts 12a, 12b, in particular by the rotary axis dA and parallel to the sections of the articulated parts 12a, 12b running be-tween the rotary axis dA and the handle parts 14a, 14b.

A ratchet lock 40 is arranged between both articulated parts 12a, 12b, in particular between both handle parts 14a, 14b, by means of which ratchet lock both articulated parts 12a, 12b can be fixed in a position relative to each other. The ratchet lock 40 can be released by means of a pivotably mounted release lever 41.

Whilst the articulated parts 12a, 12b are arranged substantially parallel to each other in the region between the rotary axis dA and the handle parts 14a, 14b, they proceed in a curve in the region between the rotary axis dA and the retracting elements 16a, 16b and together form a U shape in particular. Thus, when the retractor 10 is used, the articulated parts 12a, 12b do not obstruct the view of the operation site.

An arm 19a, 19b is arranged on at least one, in the present embodiment on both, of the articulated parts 12a, 12b, between the handle parts 14a, 14b and the retracting elements 16a, 16b, in particular in the region between the rotary axis dA and the retracting elements 16a, 16b, preferably, however, closer to the rotary axis dA than the retracting elements 16a, 16b, such that said arm is directed outwards and thus in particular points away from the respective other articulated part 12b, 12a. The arms 19a, 19b lie in the plane spanned by the sections 18a, 18b. Advantageously, both arms 19a, 19b lie on a straight line, which is arranged in particular vertically to the symmetrical axis S of the retractor 10. The arms 19a, 19b are particularly rigid, and advantageously are integrally disposed at the respective articulated parts 12a, 12b.

A device for attaching a clamping arm 20 is arranged at the free end of the arms 19a, 19b.

The clamping arm 20 is attached such that the clamping arm 20 is arranged on the arm 19a, 19b rotatably mounted about a pivotal axis S1A. The pivotal axis S1A is spaced in the plane at a distance a from the articulated part 12a, 12b, which corresponds approximately to the length of the arm 19a, 19b. This means that the attachment point of the clamping arm 20 is displaced further outwards, which allows greater bending radiuses of the clamping arms 20 in order to achieve a desired position within the U-shaped region between the articulated parts 12a, 12b as well as a shortening of the clamping arms 20.

A sprocket 50 with teeth running radially outwards on the front side is arranged in particular on the arm 19a, 19b for attaching the clamping arm. A bore hole 52, which has an internal screw thread, is axially arranged in the sprocket 50.

The clamping arm 20 has a first sprocket 24, which has teeth running radially outwards on the front side thereof, and can be attached to the sprocket 50. The sprocket 24 has an axial bore hole 25 in particular, which is arranged flush with the arms 19a, 19b with the bore hole 52 of the sprocket 50. Both sprockets 24, 50 can be positioned at various angles relative to each other and consequently a flexible alignment of the clamping arm 20 is possible.

The clamping arm 20 can be attached by guiding a screw 53 through the bore hole 25 and the bore hole 52 and, screwing it into bore hole 52 for example. In order to be able to tighten the screw 53 without further devices, said screw preferably has a lever 54 on the head thereof, which facilitates the tightening of the screw 53 and advantageously is pivotably arranged about an axis in order to fold the lever 54 away and arrange it in a space-saving manner if it is not required.

The clamping arm 20 can have a second sprocket 26, in addition to the first sprocket 24, which is arranged parallel to the first sprocket 24 and has teeth running radially on its front side, which point in the opposite direction to the direction of the teeth of the first sprocket 24. Firstly, this enables an attachment of the clamping arm 20 to an arm 19a, 19b rotated 180° about the longitudinal axis of said clamping arm 20 and secondly, the reciprocal arrangement of a clamping arm 20 both on one arm 19a and on the other arm 19b. The toothing of the sprockets 50, 24, 26 is selected as fine here such that when the sprockets 24, 26 are rotated against the sprocket 50 about a tooth, the degree of rotation is only slight.

The clamping arm 20 has a plurality of tensioning elements 22, which can each have a cylindrical section 22a and a semi-spherical section 22b. Here the spherical section 22b of one of the tensioning elements 22 engages in the cylindrical section 22a of one of the other tensioning elements 22. The semi-spherical section 22b enables a tipping of the adjacent tensioning elements 22 in any direction as well rotation of the adjacent tensioning elements 22 about the longitudinal axis thereof running through the cylindrical section 22a. The tensioning elements 22 are threaded onto a traction cable (not shown), which is attached at one end to a distal tensioning element 29, which forms the distal end of the clamping arm 20, whilst the other end is attached to a clamping device 23 at the proximal end of the clamping arm 20. In order to thread the tensioning elements 22, said tensioning elements have a continuous longitudinal opening and are configured more particularly as hollow pieces. The clamping device 23 has a pivoted lever in particular, with which the length of the traction cable remaining in the clamping arm 20 is shortened during pivoting, and in this manner the clamping arm 20 is tightened and the tensioning elements 22 are fixed in their position relative to each other. In one embodiment, the tensioning elements 22 have at least one, in the example, four windows 22c, distributed equidistantly over the area, more particularly in the cylindrical section 22a, which enables easy cleaning of the tensioning elements 22. The ten-dons 22 have a length l and a diameter d, wherein the length l can be 12 mm, for example, and the diameter d can be 8 mm.

A holder 30 for a brain spatula 60 can be arranged on the distal end of the clamping arm 20, more particularly on the distal tensioning element 29. The holder 30 has two clamping jaws 31, 32, be-tween which the brain spatula 60 can be gripped, for example spring loaded or after tightening a locking screw 36. The holder 30 has a bearing surface 34 with which it abuts the distal end of the clamping arm 20.

In one embodiment, the distal end of the clamping arm 20 is beveled, for example at an angle of 45° to the longitudinal axis of the distal tensioning element 29. The bearing surface 34 of the holder 30 can be rigidly connected to the distal end of the clamping arm 20, or, alternatively, rotatably mounted about an axis which runs vertically to the bearing surface 34. When the holder 30 is turned about said axis, the brain spatula 60 held between the clamping jaws 31, 32 can be aligned in various spatial directions. The locking screw 36 can form the pivotal axis and, once the desired alignment between the holder 30 and the distal end of the clamping arm 20 has been determined by fixing both the holder 30 to the distal end of the clamping arm 20 in the desired position, at the same time fix the brain spatula 30 between both clamping jaws 31, 32. The clamping jaws 31, 32 can be bent at right angles which enables a more compact configuration.

The brain spatula 60 can be made from a shape memory material, such as nickel titanium, in order to enable flexible use during operation and also reusability after cleaning.

LIST OF REFERENCE NUMBERS

10 Retractor
12a, b Articulated part
14a, b Handle part
16a, b Retracting element
18a, b Section
19a, b Arm
20 Clamping arm
22 Tensioning element
22a Cylindrical section
22b Semi-spherical section
22c Window
23 Clamping device
24 First sprocket
26 Second sprocket
29 Distal tensioning element
29a Beveled surface
30 Holder
31 Clamping jaw
32 Clamping jaw
34 Bearing surface
36 Locking screw
40 Ratchet lock
41 Release lever
50 Sprocket
52 Bore hole
53 Screw
54 Lever
60 Brain spatula
dA Rotary axis
S1A Pivotal axis
a Distance
Length
d Diameter
S Symmetrical axis The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable equivalents.

I claim:

1. A retractor, comprising two articulated parts that can be pivoted relative to each other about a rotary axis, wherein each articulated part has a handle part on the proximal end and a retracting element on the distal end, wherein a section of each articulated part spans a plane and wherein a clamping arm is arranged on each the articulated parts, wherein the clamping arm has a plurality of tensioning elements, which are threaded onto a traction cable and which engage with each other in sections and can be tilted and/or rotated relative to each other, wherein each is pivotably arranged about a pivotal axis and the pivotal axis is connected to the articulated part by means of a fixed arm arranged in a plane, wherein the arm is aligned outwards from and substantially perpendicular to the articulated part and consequently the pivotal axis is positioned in the plane at a distance from the articulated part, and wherein each of the pivotal axes and the rotary axis are substantially aligned when the handle parts are in a converged orientation.

2. The retractor of claim 1, wherein the tensioning elements have a length and a diameter, wherein the ratio between the diameter and the length is between 1:1 and 2:3.

3. The retractor of claim 1, wherein each tensioning element has a cylindrical section and a semi-spherical section, wherein a semi-spherical section of a tensioning element engages in a cylindrical section of another tensioning element.

4. The retractor of claim 1, wherein the tensioning elements have one or more windows, which windows are arranged in the cylindrical section.

5. The retractor of claim 1, wherein the clamping arm has a sprocket running about the pivotal axis, which can be attached to a sprocket arranged on the arm running about the pivotal axis.

6. The retractor of claim 1, wherein the clamping arm has two sprockets arranged parallel to each other running about the pivotal axis, and the teeth of said sprockets point in opposite directions.

7. The retractor of claim 1, further comprising wherein a holder for a brain spatula is arranged on the distal end of the clamping arm.

8. The retractor of claim 1, wherein the distal end of the clamping arm is beveled and a bearing surface of a holder abuts the beveled surface of the distal end of the clamping arm and is arranged in a rotatably mounted manner about a rotary axis which vertically intersects the bearing surface.

9. The retractor of claim 1, wherein a brain spatula is made from nickel titanium or another known shape memory material.

10. The retractor of claim 1, wherein a locking mechanism, preferably a ratchet lock, is arranged between both articulated parts.

11. The retractor of claim 1, wherein a locking mechanism, preferably a ratchet lock, is arranged between both handle parts.

12. The retractor of claim 1, wherein the retracting element is configured as retracting prongs and is arranged at an angle to the plane.

* * * * *